Figure 1:
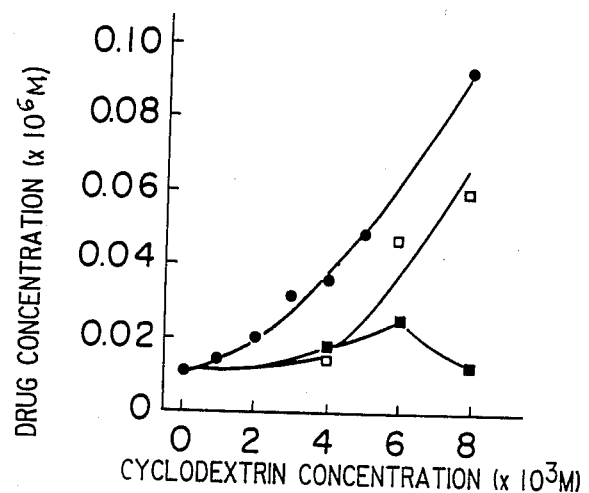

United States Patent [19]

Kondo et al.

[11] Patent Number: 4,849,425
[45] Date of Patent: * Jul. 18, 1989

[54] READILY ABSORBABLE PHARMACEUTICAL COMPOSITION

[75] Inventors: Nobuo Kondo, Daito; Tsunetaka Nakajima, Kashiwara; Masahiro Watanabe, Akashi; Kazumasa Yokoyama, Toyonaka; Tadakazu Suyama, Kyoto; Takahiro Haga, Kusatsu; Nobutoshi Yamada; Hideo Sugi, both of Moriyama; Toru Koyanagi, Kyoto, all of Japan

[73] Assignees: Ishihara Sangyo Kaisha Ltd.; The Green Cross Corporation, both of Osaka, Japan

[*] Notice: The portion of the term of this patent subsequent to Feb. 23, 2005 has been disclaimed.

[21] Appl. No.: 824,088

[22] Filed: Jan. 30, 1986

[30] Foreign Application Priority Data

Feb. 20, 1985 [JP] Japan .................................. 60-32365
Mar. 8, 1985 [JP] Japan .................................. 60-44737

[51] Int. Cl.$^4$ .................. A61K 31/505; A61K 31/715
[52] U.S. Cl. ..................................... 514/274; 514/58; 514/946
[58] Field of Search .................. 514/594, 58, 269, 351, 514/772, 786, 274, 946

[56] References Cited

U.S. PATENT DOCUMENTS 4,503,045 3/1985 Fujii et al. .............................. 514/25

FOREIGN PATENT DOCUMENTS 0164694 12/1985 European Pat. Off. .
0056312 5/1978 Japan .................................... 514/274
0109953 9/1978 Japan .

OTHER PUBLICATIONS

Hackh's Chemical Dictionary, 4th Ed., 1972, p. 381.
*Formulary of Liquid Oral Products,* Altas Chemical Industries, Inc., 1962, p. 34.
Patents Abstracts of Japan, vol. 6, No. 202, Oct., 1982, JP-A-57 109 721 (Ishihara Sangyo K.K.).

Primary Examiner—Douglas W. Robinson
Assistant Examiner—R. Kearse
Attorney, Agent, or Firm—Oblon, Spivak, McClelland, Maier & Neustadt

[57] ABSTRACT

A pharmaceutical composition comprising a benzoyl urea compound having the formula:

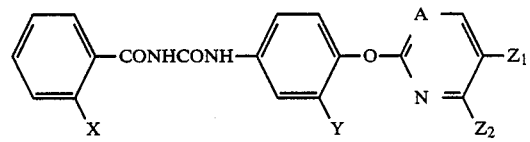

wherein X is a nitro group, Y is a chlorine atom, $Z_2$ is a hydrogen atom, $Z_1$ is a halogen atom, and A is a nitrogen atom, and at least one member selected from the group consisting of a cyclodextrin, a polyethylene glycol and a refined oil.

20 Claims, 2 Drawing Sheets

READILY ABSORBABLE PHARMACEUTICAL COMPOSITION

The present invention relates to an antitumour pharmaceutical composition containing a benzoyl urea compound as the main component. More particularly, the present invention relates to a pharmaceutical composition whereby the absorbability of an antitumour benzoyl urea compound of the formula:

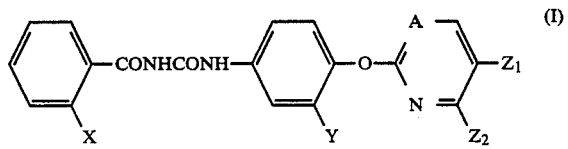

wherein X is a halogen atom or a nitro group, each of Y and $Z_2$ is a hydrogen atom or a halogen atom, $Z_1$ is a halogen atom or a trifluoromethyl group, and A is a =CH—group or a nitrogen atom, through e.g. mucous membranes of e.g. the gut, improved.

The benzoyl urea compounds of the formula I are known to have excellent antitumour activities (Japanese Unexamined Patent Publication No. 109721/1982). However, these compounds are hardly soluble in water, and accordingly their absorbability through e.g. the gut is poor. Therefore, in order to obtain adequate antitumour activities, it is necessary to increase the dose, whereby there is a possible danger of adverse effects due to the excessive administration.

It is an object of the present invention to provide a pharmaceutical composition whereby the absorbability of the benzoyl urea compound of the formula I through the skins or mucous membranes of the gut, rectum, etc., is improved.

The present inventors have studied various additives with an aim to improve the absorbability of the benzoyl urea compound of the formula I through the skins or mucous membranes of the gut, rectum, etc., and have finally found that certain specific substances, i.e. cyclodextrins, polyethylene glycols and refined oils, are capable of improving the absorbability of the benzoyl urea compound of the formula I through e.g. mucous membranes, particularly, from the gut and rectum.

Thus, the present invention provides a pharmaceutical composition comprising a benzoyl urea compound of the formula I and at least one member selected from the group consisting of a cyclodextrin, a polyethylene glycol and a refined oil.

Now, the present invention will be described in detail with reference to the preferred embodiments.

In the accompanying drawings, FIG. 1 is a graph showing the solubility of Compound No. 1 in aqueous solutions of various cyclodextrins, wherein ■ designates α-type cyclodextrin, □ designates γ-type cyclodextrin and ● designates β-type cyclodextrin.

Figure 2:
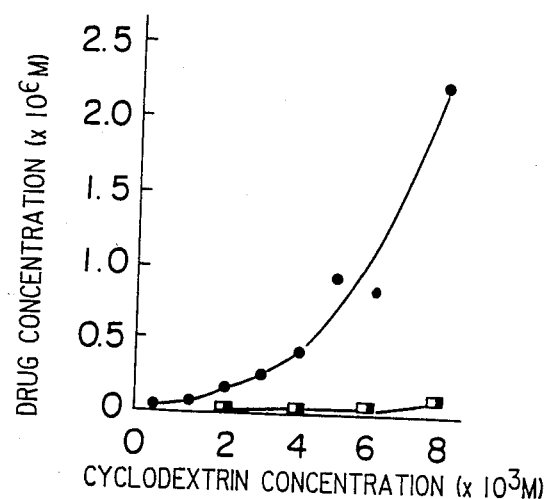

FIG. 2 is a graph showing the solubility of Compound No. 2 in aqueous solutions of various cyclodextrins, wherein ■, □ and ● are as defined in respect of FIG. 1.

Figure 3:
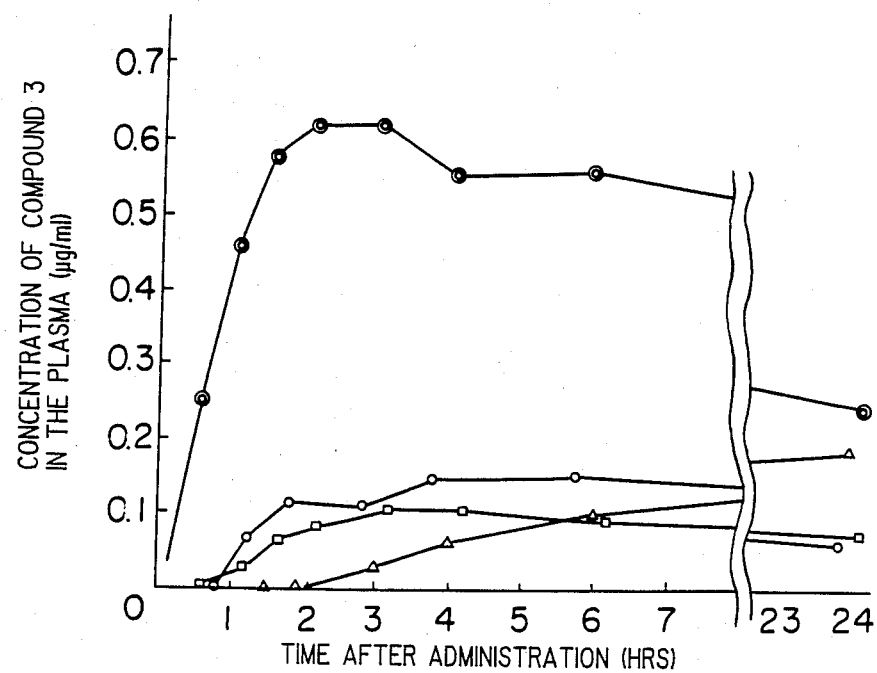

FIG. 3 is a graph showing the change with time of the concentration of Compound No. 3 in the plasma when the compound dispersed in various cyclodextrins was orally administered, wherein ○ designates the control, △ designates β-type cyclodextrin having a concentration of 1.7%, ◉ designates dimethyl β-type cyclodextrin having a concentration of 40%, and □ designates dimethyl β-type cyclodextrin having a concentration of 2%.

Figure 4:
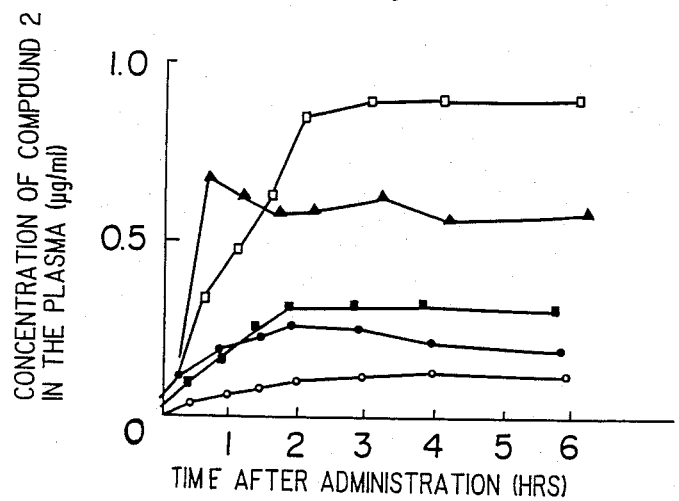

FIG. 4 is a graph showing the change with time of the concentration of Compound No. 2 in the plasma when the compound dispersed in various solvents was orally administered, wherein ○ designates the control, ● designates polyoxyethylene hardened castor oil, ■ designates Tween 80, □ designates polyethylene glycol 400, and □ designates dimethyl β-type cyclodextrin.

In this specification, the halogen atom is preferably a chlorine atom or a bromine atom.

The following compounds may be mentioned as typical examples of the benzoyl urea compound of the formula I.

Compound No. 1: (Melting point: 182–185° C.)

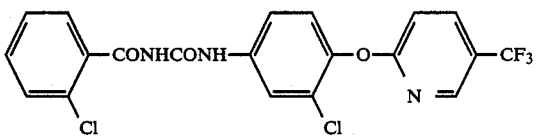

Compound No. 2: (Melting point: 235–238° C.)

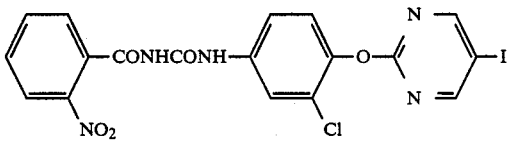

Compound No. 3: (Melting point: 229–231° C.)

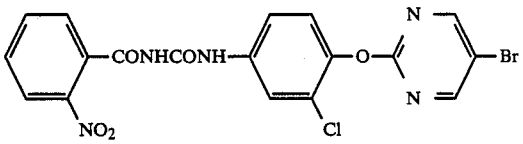

Compound No. 4: (Melting point: 207–208° C.)

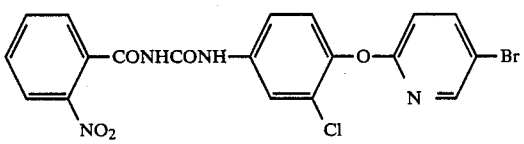

The benzoyl urea compounds of the present invention may be prepared, for instance, by the following process:

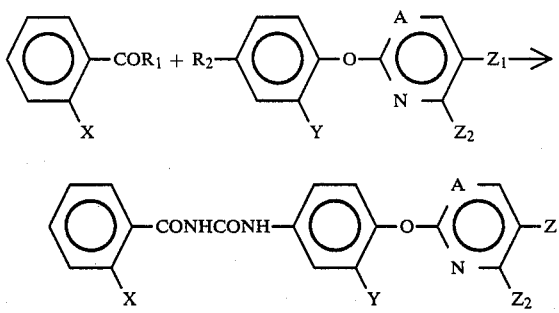

wherein X, Y, $Z_1$, $Z_2$ and A are as defined above, and each of $R_1$ and $R_2$ is an isocyanate group or an amino group, provided that $R_1$ and $R_2$ are different from each other.

Specifically, the following processes may be mentioned.

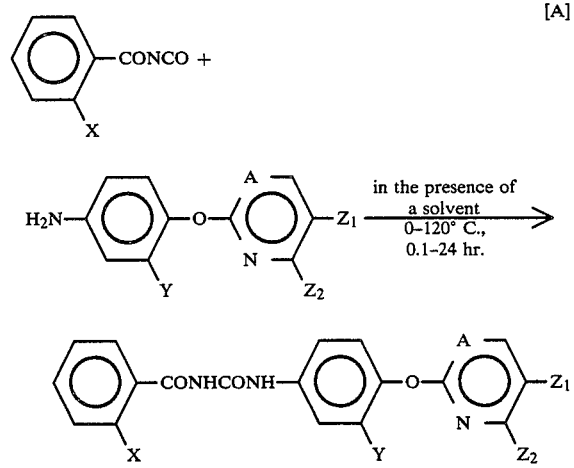

[A]

wherein X, Y, $Z_1$, $Z_2$ and A are as defined above.

As the solvent to be used in the above reaction, octane, benzene, toluene, xylene, monochlorobenzene, dimethylsufoxide or ethyl acetate may be mentioned.

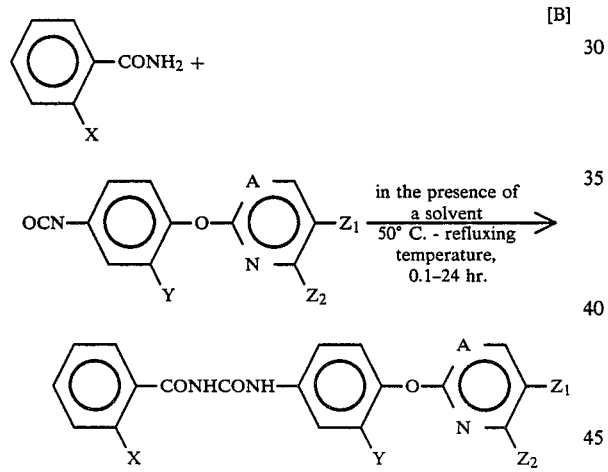

[B]

wherein X, Y, $Z_1$, $Z_2$ and A are as defined above.

The solvent to be used in the above reaction is the same as one used in the reaction [A].

The aniline compound or the phenyl isocyanate compound used as the starting material in each of the above reactions, may be prepared, for instance, by the following processes.

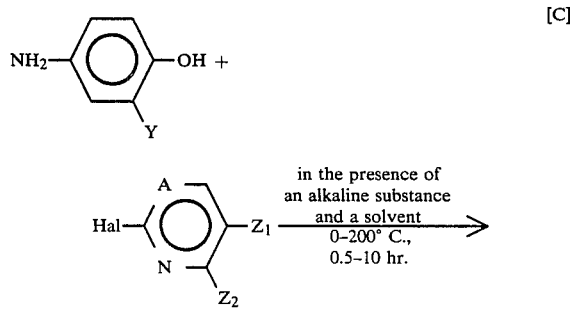

[C]

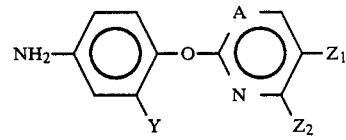

wherein Hal is a halogen atom, and Y, $Z_1$, $Z_2$ and A are as defined above.

As the alkaline substance to be used in the above reaction, sodium hydroxide, potassium hydroxide, sodium carbonate or potassium carbonate may be mentioned. As the solvent, there may be mentioned an aprotic polar solvent such as dimethylsulfoxide, dimethylformamide, hexamethylphosphoroamide or sulfolane, or a ketone such as acetone, methyl ethyl ketone or methyl isobutyl ketone.

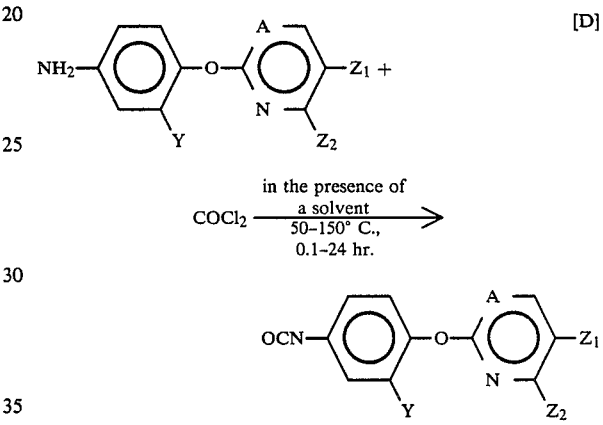

[D]

wherein Y, $Z_1$, $Z_2$ and A are as defined above.

As the solvent to be used in the above reaction, a solvent inert to phosgene, such as toluene, xylene, monochlorobenzene, ethyl acetate or dioxane, may be mentioned.

Now, a specific example for the preparation of a benzoyl urea compound to be used in the present invention, will be presented.

SYNTHETIC EXAMPLE

Synthesis of Compound No. 3:
N-(2-nitrobenzoyl)-N'-[4-(5-bromo-2-pyrimidinyloxy)-3-chlorophenyl]urea (1) Into a flask, 10.0 g of 5-bromo-2-chloropyrimidine, 7.42 g of 4-amino-2-chlorophenol, 14.26 g of potassium carbonate and 100 ml of dimethylsulfoxide were introduced, and reacted in a nitrogen atmosphere at 120° C. for 2.5 hours under stirring. After the completion of the reaction, the product was poured into water, and extracted with ethyl acetate. The extract was washed with water and a saturated sodium chloride aqueous solution, dried over anhydrous sodium sulfate, and then purified by silica gel column chromatography, whereby 12.26 g of oily 4-(5-bromo-2-pyrimidinyloxy)-3-chloroaniline was obtained.

(2) Into a flask, a solution obtained by dissolving 12.26 g of the above 4-(5-bromo-2-pyrimidinyloxy)-3-chloroaline in 45 ml of dioxane, was introduced, and a solution obtained by dissolving 8.64 g of 2-nitrobenzoyl isocyanate in 45 ml of dioxane, was dropwise added thereto, and then the mixture was reacted at room temperature of 5 hours. After the completion of the reaction, the product was poured into water, subjected to filtration and washed with hot water. The crystals thereby obtained were washed with ethyl acetate, methylene chloride and methanol, to obtain 13.5 g of the desired product having a melting point from 229° to 231° C.

As the cyclodextrins which may be employed in the present invention, dialkylated cyclodextrins (such as dimethylcyclodextrin) or trialkylated cyclodextrins (such as trimethylcyclodextrin) may be mentioned. The cyclodextrins may be α-type, β-type or γ-type. It is preferred to employ a dimethyl β-type cyclodextrin. The cyclodextrin is incorporated usually in an amount of from 0.01 to 100 parts by weight, preferably from 0.1 to 10 parts by weight, relative to 1 part by weight of the benzoyl urea compound of the formula I. This combination is particularly preferred for the preparation of a solid formulation, and suitable for use for preparation of tablets, granules or suppositories.

As the polyethylene glycol, it is usual to employ a polyethylene glycol having an average molecular weight of from 200 to 20,000, preferably from 200 to 4,000. The concentration of the benzoyl urea compound of the formula I in the polyethylene glycol is adjusted usually at a level of from 5 to 50 mg/ml, preferably from 10 to 30 mg/ml. This composition is suitable for the formulation for rectal administration such as a suppository, or for the formulation of external application such as an ointment.

As the refined oil, there may be mentioned vegetable oils such as soybean oil, safflower oil, sesame oil or olive oil, and glycerides such as a medium-chain length fatty acid triglycerides (wherein the medium-chain length fatty acids are preferably straight chained or branched fatty acids having from 8 to 10 carbon atoms, such as caprylic acid or capric acid) [for example, ODO ® (manufactured by Nisshin Seiyu K.K.), Conconard RK, MT (manufactured by Kao Food K.K.)]. The refined oil is an oil purified to such an extent that it is useful for a pharmaceutical. The refined oil is incorporated in such an amount that the concentration of the benzoyl urea compound of the formula I in the refined oil will be from 5 to 500 mg/ml, preferably from 20 to 200 mg/ml. This composition is suitable for the preparation of soft capsules. In the case where the refined oil is employed, it is possible to further improve the solubility by incorporating various surfactants. As such surfactants, nonionic surfactants are preferred, such as, a polyoxyethylene-polyoxy propylene copolymer (pluronic), a glycerin fatty acid ester, a sorbitol fatty acid ester, a propylene glycol fatty acid ester, a sucrose fatty acid ester, a polyethylene glycol fatty acid ester, Tween 80 or a polyoxyethylene hardened castor oil. Further, as an ionic surfactant, sodium lauryl sulfate may be employed. The surfactant is incorporated usually in an amount of from 1 to 50% (weight/volume), preferably from 2 to 10% (weight/volume) of the total amount.

The pharmaceutical composition of the present invention may be formulated in accordance with the conventional methods for formulations. For instance, a liquid formulation may be filled in suitable capsules to obtain capsule drugs. Further, the liquid formulation may be freeze-dried or spray-dried to obtain a dried formulation. The dried formulation may be formed into tablets, capsules, enteric drugs, granules, powders, suppositories, ointments, etc. by the conventional methods for drug formulations.

As will be shown in Test Examples 1 and 2, the cyclodextrins increase the solubility of the benzoyl urea compound of the formula I in water, and thus they are believed to increase the absorption of the benzoyl urea compound by the gut, etc.

As will be shown in Test Examples 3 and 4, by suspending the benzoyl urea compound of the formula I in aqueous solutions of cyclodextrins, the concentration of the benzoyl urea compound of the formula I in the plasma after the oral administration is distinctly higher as compared with the control.

Further, also in the case where the polyethylene glycols or refined oils are incorporated, it is likewise evident that the absorption of the benzoyl urea compound of the formula I by the gut is facilitated.

By using the pharmaceutical composition of the present invention, it is possible to reduce the dose of the benzoyl urea compound of the formula I and thus to reduce the side effects or the pain to the patient when it is administered.

Thus, the pharmaceutical composition of the present invention makes it possible to provide an effective formulation of the benzoyl urea compound of the formula I which has not been possible by the conventional method for formulations, and thus opens a new way for medical and clinical developments.

TEST EXAMPLE 1 (SOLUBILITY)

0.1 μmol of Compound No. 1 or No. 2 was added to 1 ml of an aqueous solution of each cyclodextrin with a concentration of from 0 to 8 mM, and the mixture was shaken at 25° C. for 100 hours. After completion of the shaking, the mixture was filtered through a millipore filter of 0.45 μm to obtain a filtrate. The dissolved Compound No. 1 or No. 2 was quantitatively analyzed by a high speed liquid chromatography under the conditions identified below, and the solubility was obtained. The obtained solubilities are shown in FIGS. 1 and 2.

OPERATIONAL CONDITIONS FOR THE LIQUID CHROMATOGRAPHY

Separation column: As the packing material, octadecylated silica gel was filled in a stainless steel tube having an internal diameter of from 0.39 to 4.6 mm and a length of from 100 to 300 mm.
Column temperature: 30° C.
Mobile phase: Mixture of acetonitrile-water (the mixing ratio was adjusted so that the eluting time of the drug becomes from 5 to 10 minutes).
Flow rate: 1 ml/min.
Wave length for detection: 265 nm

TEST EXAMPLE 2 (SOLUBILITY)

7.5 mg of Compound No. 3 was added to 1 ml of an aqueous solution of each cyclodextrin at various concentrations or to 1 ml of polyethylene glycol 400, and the solubility of Compound No. 3 at 25° C. was obtained in the same manner as the Test Example b 1. The results thereby obtained are shown in Table 1.

TABLE 1

| Additives | Concentrations (mg/ml) | Solubility of Compound No. 3 (μg/ml) |
|---|---|---|
| Aqueous solution containing no additives | — | 0.024 |
| α-Type cyclodextrin | 14.6 | 0.164 |
| Dimethyl α-type cyclodextrin | 17.5 | 0.294 |

TABLE 1-continued

| Additives | Concentrations (mg/ml) | Solubility of Compound No. 3 (μg/ml) |
|---|---|---|
| β-Type cyclodextrin | 17.0 | 1.64 |
| Dimethyl β-type cyclodextrin | 20.0 | 24.1 |
| Dimethyl β-type cyclodextrin | 140 | 5180 |
| Dimethyl β-type cyclodextrin | 500 | 7440 |
| Trimethyl β-type cyclodextrin | 21.4 | 1.00 |
| Trimethyl β-type cyclodextrin | 100 | 13.4 |
| Trimethyl β-type cyclodextrin | 200 | 30.4 |
| Polyethylene glycol 400 | 100% | 7500 |

TEST EXAMPLE 3 (ABSORBABILITY THROUGH THE GUT)

20 mg of Compound No. 3 was taken into a mortar, and 5 ml of an aqueous solution containing 1.7% of β-type cyclodextrin or 2% or 40% of dimethyl β-type cyclodextrin was added under stirring to obtain a suspension of Compound No. 3. The suspension was orally administered by an oral sonde to a group of three Wistar male rats (body weight: 200–250g). The dose of Compound No. 3 was 20 mg/kg rat body weight. Further, Compound No. 3 was likewise suspended in an aqueous solution containing 0.5% of sodium salt of carboxymethyl cellulose, and the suspension was used as the control (○ in FIG. 3). After the administration, the blood was periodically sampled, and the plasma was separated. After the removal of protein by acetonitrile, Compound No. 3 in the plasma was quantitatively analyzed by a high speed liquid chromatography as shown in Test Example 1. The change with time of the concentration of Compound No. 3 in the plasma after the administration is shown in FIG. 3.

In the case of 40% dimethyl β-type cyclodextrin, the concentration in the plasma was as high as about 3.5 times the concentration obtained by the control.

TEST EXAMPLE 4 (ABSORBABILITY THROUGH THE GUT)

The changes with time of the concentration of Compound No. 3 in the plasma after the oral administration were studied in the same manner as in Test Example 3 by using an aqueous solution of 10% (weight/volume) Polysolvate 80 (Tween 80, manufactured by Nakayai Kagaku K.K.), 10% (weight/volume) polyoxyethylene hardened caster oil 60 (manufactured by Nikko Chemical K.K.), 100% polyethylene glycol 400 or 50% (weight/volume) dimethyl β-type cyclodextrin, as the dispersing solvent for Compound No. 3, and an aqueous solution of 0.5% (weight/volume) sodium salt of carboxymethyl cellulose, as the control. The results are shown in FIG. 4. The concentration of Compound No. 3 in the plasma was about 7.5 times in the case of dimethyl β-type cyclodextrin and about 5 times in the case of polyethylene glycol 400, as compared with the control.

TEST EXAMPLE 5 (ABSORBABILITY THROUGH THE GUT)

The changes with time of the concentration of Compound No. 3 in the plasma after the oral administration were studied in the same manner as in Test Example 3 by using an aqueous solution of 10% (weight/volume) hydroxypropyl cellulose (HPC-L, manufactured by Nippon Soda Co., Ltd.), 2.5% (weight/volume) methyl cellulose (Metrose SM 15, manufactured by Shin-Etsu Chemical Co., Ltd.), 10% (weight/volume) hydroxypropylmethyl cellulose (Metrose TC5R, manufactured by Shin-Etsu Chemical Co., Ltd.), 2.5% (weight/volume) sodium salt of carboxymethyl cellulose (manufactured by Wako Junyaku K.K.), 10% (weight/volume) sucrose fatty acid ester (P1570, manufactured by Hishito K.K.) or 10% (weight/volume) pluronic F 68 (manufactured by Asahi Denka Kogyo K.K.), as an aqueous dispersing solvent for Compound No. 3, and medium-chain length fatty acid triglyceride (ODO, manufactured by Nisshin Seiyu K.K.), ODO containing 5% (weight/volume) sucrose fatty acid ester (S-370F, manufactured by Hishito K.K.), or a refined soybean oil (The Green Cross Corporation) or refined sesame oil (Takemoto Yushi K.K.) containing 5% (weight/volume) of S-370F, as a non-aqueous dispersing solvent, and an aqueous solution of 50% (weight/volume) dimethyl β-type cyclodextrin and an aqueous solution of 0.5% (weight/volume) sodium carboxymethyl cellulose, as the control. The results are shown in Table 2.

Among the aqueous dispersing solvents, 50% (weight/volume) dimethyl β-type cyclodextrin showed the highest absorption; and among the non-aqueous dispersing solvents, the refined soybean oil or refined sesame oil containing 5% (weight/volume) sucrose fatty acid ester showed a high absorption almost equal to dimethyl β-type cyclodextrin. Further, ODO containing 5% (weight/volume) Pluronic F32 showed a high absorption.

TABLE 2

| | Concentration in the plasma (μg/ml) | | | |
|---|---|---|---|---|
| | 1 hr | 3 hrs | 5 hrs | 24 hrs |
| 10% (weight/volume) hydroxypropyl cellulose | 0.05 | 0.12 | 0.11 | 0.04 |
| 2.5% (weight/volume) methyl cellulose | 0.06 | 0.11 | 0.11 | 0.03 |
| 10% (weight/volume) hydroxypropylmethyl cellulose | 0.14 | 0.31 | 0.28 | 0.10 |
| 2.5% (weight/volume) sodium salt of carboxymethyl cellulose | 0.04 | 0.11 | 0.09 | 0.09 |
| 10% (weight/volume) sucrose fatty acid ester | 0.04 | 0.18 | 0.18 | 0.24 |
| 10% (weight/volume) Pluronic F68 | 0.11 | 0.19 | 0.23 | 0.12 |
| Medium-chain length fatty acid triglyceride (ODO) | 0.12 | 0.17 | 0.21 | 0.24 |
| 5% (weight/volume) sucrose fatty acid ester/ODO | 0.06 | 0.18 | 0.20 | 0.22 |
| 5% (weight/volume) sucrose fatty acid ester/refined soybean oil | 0.12 | 0.50 | 0.55 | 0.39 |
| 5% (weight/volume) sucrose fatty acid ester/refined sesame oil | 0.14 | 0.49 | 0.57 | 0.37 |
| 5% (weight/volume) Pluronic F31/ODO | 0.10 | 0.20 | 0.22 | 0.47 |
| 0.5% (weight/volume) sodium salt of carboxymethyl cellulose | 0.03 | 0.10 | 0.15 | 0.01 |
| 50% (weight/volume) Dimethyl β-type cyclodextrin | 0.28 | 0.58 | 0.49 | 0.36 |

TEST EXAMPLE 6

A Witepsol W-35 suppository (weight: about 45 mg) comprising 1.8 mg of Compound No. 3 and 12.5% (weight/volume) of dimethyl β-type cyclodextrin, was administered to the rectum of each Wistar male rat having a body weight of about 90 g (a group of three rats). Then, the blood was periodically sampled from the jugular vein, and the concentration of Compound No. 3 in the plasma was measured. To a control group, a suppository contained no cyclodextrin was administered. The results are shown in Table 3. It is evident that by the addition of dimethyl β-type cyclodextrin, the absorbability of Compound No. 3 increased.

TABLE 3

| | Concentration in the plasma (μg/ml) | | | | |
|---|---|---|---|---|---|
| | 0 | 0.5 hr | 1 hr | 2 hrs | 4 hrs |
| Control | 0 | 0.04 | 0.08 | 0.11 | 0.09 |
| Dimethyl β-type cyclodextrin | 0 | 0.32 | 0.48 | 0.94 | 0.99 |

TEST EXAMPLE 7

The capsules prepared in Example 3 corresponding to 20 mg/kg of Compound No. 3 were orally administered to three beagle dogs (male: body weight: 5 kg). Then, the blood was periodically sampled from the branchium vein, and the concentration of Compound No. 3 in the plasma was measured. To the control group, a suspension of Compound No. 3 (20 mg/ml) in an aqueous solution containing 0.5% of sodium salt of carboxymethyl cellulose was administered. The results are shown in Table 4. It is evident that the present invention, the absorbability of Compound No. 3 increased.

TABLE 4

| | Concentration in the plasma (μg/ml) | | | | |
|---|---|---|---|---|---|
| | 0 | 0.5 hr | 1 hr | 2 hrs | 4 hrs |
| Control | 0 | 0.03 | 0.07 | 0.10 | 0.09 |
| Polyethylene glycol 400 | 0 | 0.37 | 0.61 | 1.12 | 1.11 |

TEST EXAMPLE 8

The acute toxicity, the dose and the administration method were studied with respect to the formulations obtained by the present invention.

ACUTE TOXICITY $BDF_1$ mice (male, female, 25-27 g) or SD rats (male, female, 250-270 g) were used in a group of 10 animals. To these animals, the formulations prepared in Examples 1 to 6 were orally administered in the form of a liquid suspension, at a dose of 50 mg/kg of the benzoyl urea compound of the formula I. The animals were observed for 7 days, whereby no instance of death was observed. On the other hand, the same results were obtained when the substrate material only or the benzoyl urea compound of the formula I only was suspended in water and orally administered.

DOSE

The dose may be varied depending upon the subject to be treated, the degree of the disease or other conditions for administration, and can not simply be prescribed. However, a daily dose is usually from about 0.1 to about 100 mg/kg of the active ingredient.

ADMINISTRATION METHOD

The pharmaceutical composition of the present invention may be administered through oral, rectal or cutaneous route in various formulations as mentioned above

TEST EXAMPLE 9

The pharmacological activities of the pharmaceutical compositions of the present invention were studied. Among the formulations of Examples 1 to 6, the results of the study on the formulation of Example 3 are shown in Table 5.

To $BDF_1$ mice (male, 28-22 g), L-1210 leukemia cells were intraperitoneally inoculated in an amount of $1 \times 10^6$ cells/mouse. One day later and 4 days later, a test drug was orally administered. It was difficult to administer the drug in the final formulation form, and therefore Compound No. 3, polyethylene glycol 400 and the substrate were mixed and administered to each mouse in the form of a liquid suspension in an amount of 0.5 ml. Thereafter, the mice was observed for survival or death. As a result, the antitumour activities of Compound No. 3 was distinctly observed only when it was administered together with the substance specified in the present invention. Within the dose range of Compound No. 3 at this time, no antitumour activities were observed when polyethylene glycol 400 was absent. Namely, the results indicate the transfer of Compound No. 3 from the gut into the blood in Test Example 7, and thus reflect an improvement in the absorbability of Compound No. 3 by the composition of the present invention.

The improvement in the absorbability of the benzoyl urea compound of the formula I through the gut by the readily absorbable pharmaceutical composition of the present invention (see Test Examples 3, 4 and 5), is believed to substantially contribute to the effective antitumour activities of the compound.

TABLE 5

| Administered formualtion* | T/C (%)** |
|---|---|
| Polyethylene glycol 400 + substrate + Compound No. 3 | |
| Dose of Compound No. 3 (mg/kg) | |
| 50 | 95 |
| 25 | 183 |
| 12.5 | 134 |
| 6.25 | 120 |
| Substrate + Compound No. 3 | |
| Dose of Compound No. 3 (mg/kg) | |
| 50 | 103 |
| 25 | 101 |
| 12.5 | 102 |
| 6.25 | 102 |
| Polyethylene glycol 400 alone | 103 |
| Substrate only | 101 |
| Physiological sodium chloride solution (Control) | 100 |

*Formulation of Example 3

**$T/C (\%) = \frac{\text{Median survival time of test animals}}{\text{Median survival time of control animals}} \times 100$

EXAMPLE 1

1.8 mg of Compound No. 3 was dispersed under heating in a suppository substrate comprising b 90% by weight of polyethylene glycol 1000, 4% of polyethylene glycol 4000 and 6% of polyethylene glycol 400, and formed into a suppository by a suppository-forming mold.

EXAMPLE 2

1.8 mg of Compound No. 3 was dispersed under heating in a Witepsol W-35 suppository substrate (about 45 mg) containing 12.5% (weight/volume) dimethyl β-type cyclodextrin, and formed into a suppository.

EXAMPLE 3

Compound No. 3 was dissolved in polyethylene glycol 400 to bring the concentration to a level of 20 mg/ml, and soft gelatin capsules (an average weight: 600 mg) were prepared in accordance with a usual method (Tsuda Kyosuke et al., Iyaku Kaihatsu Kisokoza 11 Yakuzai Seizoho (Jo) p 347, Gigin Shokan).

EXAMPLE 4

Soft gelatin capsules were prepared in the same manner as in Example 3 except that a refined soybean oil, refined sesame oil or refined safflower oil containing 5% (weight/volume) of pluronic F31, was used instead of polyethylene glycol 400.

EXAMPLE 5

A small amount of water was added to 4 g of Compound No. 3 and 125 g of dimethyl β-type cyclodextrin, and the mixture was kneaded and granulated by an extrusion granulation method, and then packed into hard gelatin capsules to obtain a capsule drug for oral administration.

EXAMPLE 6

To the granules obtained in Example 3, 1% of magnesium stearate was added, and the mixture as compressed and tableted to obtain a tablet drug for oral administration.

EXAMPLE 7

A suppository was prepared in the same manner as in Example 1 except that Compound No. 1 was used instead of Compound No. 3.

EXAMPLE 8

A capsule drug was prepared in the same manner as in Example 5 except that Compound No. 2 was used instead of Compound No. 3.

We claim:
1. A pharmaceutical composition, comprising:
a benzoyl urea compound having the formula:

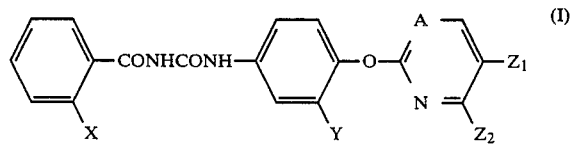

wherein X is a nitro group, Y is a chlorine atom, $Z_2$ is a hydrogen atom, $Z_1$ is a halogen atom, and A is a nitrogen atom in combination with an absorption promoting amount of at least one member selected from the group consisting of a cyclodextrin, a polyethylene glycol and a refined oil.

2. The pharmaceutical composition according to claim 1, wherein the benzoyl urea compound is N-(2-nitrobenzoyl)-N'-[3-chloro-4-(5-halogeno-2-pyrimidinyloxy) phenyl]urea.

3. The pharmaceutical composition according to claim 1, wherein the benzoyl urea compound is N-(2-nitrobenzoyl)-N'-[3-chloro-4-(5-bromo-2-pyrimidinyloxy) phenyl]urea.

4. The pharmaceutical composition according to claim 1, which comprises a benzoyl urea compound of the formula I and a cyclodextrin.

5. The pharmaceutical composition according to claim 4, wherein the cyclodextrin is a dimethyl β-type cyclodextrin.

6. The pharmaceutical composition according to claim 4, wherein the cyclodextrin is incorporated in an amount of from 0.01 to 100 parts by weight relative to one part by weight of the benzoyl urea compound.

7. The pharmaceutical composition according to claim 1, which comprises a benzoyl urea compound of the formula I and a polyethylene glycol.

8. The pharmaceutical composition according to the claim 7, wherein the polyethylene glycol has an average molecular weight of from 200 to 20,000.

9. The pharmaceutical composition according to claim 7, wherein the benzoyl urea compound is incorporated in an amount of from 5 to 50 mg relative to 1 ml of the polyethylene glycol.

10. The pharmaceutical composition according to claim 1, which comprises a benzoyl urea compound of the formula I and a refined oil.

11. The pharmaceutical composition according to claim 10, wherein the refined oil is a vegetable oil or a glyceride.

12. The pharmaceutical composition according to claim 10, wherein the benzoyl urea compound is incorporated in an amount of from 5 to 500 mg relative to 1 ml of the refined oil.

13. A pharmaceutical composition, comprising:
from 0.01 to 100 parts by weight of a dimethyl β-cyclodextrin in combination with one part by weight of a benzoyl urea compound of the formula:

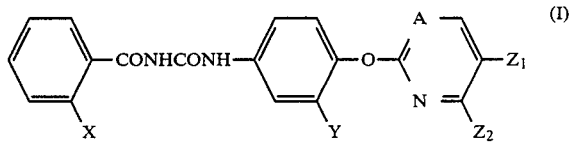

wherein X is a nitro group, Y is a chlorine atom, $Z_2$ is a hydrogen atom, $Z_1$ is a halogen atom, and A is a nitrogen atom.

14. A pharmaceutical composition, comprising:
from 5 to 50 mg of a benzoyl urea compound of the formula:

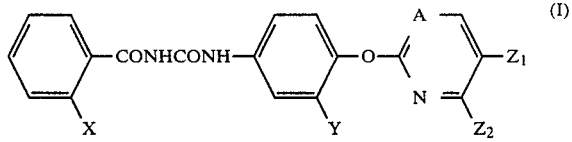

wherein X is a nitro group, Y is a chlorine atom, $Z_2$ is a hydrogen atom, $Z_1$ is a halogen atom, and A is a nitrogen atom in combination with 1 ml of a polyethylene glycol having an average molecular weight of from 200 to 20,000.

15. A pharmaceutical composition, comprising:
from 5 to 500 mg of a benzoyl urea compound of the formula:

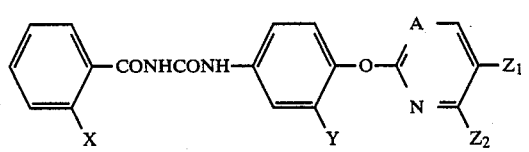

(I)

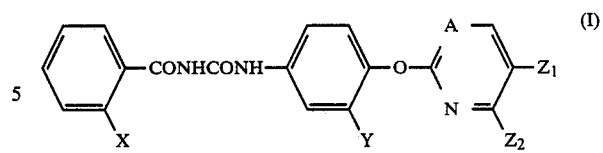

(I)

wherein X is a nitro group, Y is a chlorine atom, $Z_2$ is a hydrogen atom, $Z_1$ is a halogen atom, and Z is a nitrogen atom in combination with 1 ml of a refined oil selected from the group consisting of a vegetable oil and a glycoside, said refined oil containing from 1 to 50% (weight/volume) of a surfactant.

16. The pharmaceutical composition of claim 15, wherein said vegetable oil is soybean oil, safflower oil, sesame oil or olive oil.

17. The pharmaceutical composition of claim 15, wherein said glyceride is a $C_{8-10}$ fatty acid triglyceride.

18. A method of administering an antitumor effective amount of a benzoyl urea compound of the formula: wherein X is nitro, Y is a chlorine atom, $Z_2$ is hydrogen, $Z_1$ is halogen and A is a nitrogen atom, comprising:
administering to a subject said benzoyl urea compound in the form of a composition with an absorption promoting amount of at least one member selected from the group consisting of a cyclodextrin, a polyethylene glycol and a refined oil.

19. The method of claim 18, wherein the composition is administered orally or rectally.

20. The method of claim 18, wherein the amount of said benzoyl urea compound administered on a daily basis ranges from about 0.1 to about 100 mg/kg of body weight.

* * * * *